(12) United States Patent
Kunkel et al.

(10) Patent No.: US 7,377,897 B1
(45) Date of Patent: May 27, 2008

(54) PORTAL DEVICE

(76) Inventors: Sanford S. Kunkel, 10703 Torrey Pines Cir., Carmel, IN (US) 46032; Eric F. Dahlinger, 181 Meadowlark Dr., Hawthorn Woods, IL (US) 60047

( * ) Notice: Subject to any disclaimer, the term of this patent is extended or adjusted under 35 U.S.C. 154(b) by 663 days.

(21) Appl. No.: 10/426,213

(22) Filed: Apr. 30, 2003

Related U.S. Application Data

(60) Provisional application No. 60/377,097, filed on May 2, 2002.

(51) Int. Cl.
*A61B 1/00* (2006.01)
(52) U.S. Cl. .................... 600/184; 604/107
(58) Field of Classification Search ............ 606/185, 606/191, 194; 604/104, 107, 174; 600/201
See application file for complete search history.

(56) References Cited

U.S. PATENT DOCUMENTS

| | | | | |
|---|---|---|---|---|
| 5,275,611 A | 1/1994 | Behl | ............ | 606/198 |
| 5,312,360 A | 5/1994 | Behl | ............ | 604/164 |
| 5,356,421 A * | 10/1994 | Castro | ............ | 606/185 |
| 5,392,766 A | 2/1995 | Masterson et al. | ............ | 128/4 |
| 5,431,676 A | 7/1995 | Dubrul et al. | ............ | 606/185 |
| 5,433,708 A | 7/1995 | Nichols et al. | ............ | 604/113 |
| 5,454,790 A | 10/1995 | Dubrual | ............ | 604/104 |
| 5,540,658 A | 7/1996 | Evans et al. | ............ | 604/101 |
| 5,542,928 A | 8/1996 | Evans et al. | ............ | 604/113 |
| 5,637,097 A * | 6/1997 | Yoon | ............ | 604/174 |
| 5,653,692 A | 8/1997 | Masterson et al. | ............ | 604/113 |
| 5,814,058 A | 9/1998 | Carlson et al. | ............ | 606/185 |
| 5,820,600 A | 10/1998 | Carlson et al. | ............ | 604/167 |
| 5,827,319 A | 10/1998 | Carlson et al. | ............ | 606/191 |
| 5,836,913 A | 11/1998 | Orth et al. | ............ | 604/107 |
| 5,891,094 A | 4/1999 | Masterson et al. | ............ | 604/113 |
| 6,080,174 A | 6/2000 | Dubrul et al. | ............ | 606/185 |
| 6,197,002 B1 * | 3/2001 | Peterson | ............ | 604/164.01 |
| 6,245,052 B1 | 6/2001 | Orth et al. | ............ | 604/506 |
| 6,248,057 B1 | 6/2001 | Mavity et al. | ............ | 600/3 |
| 6,325,812 B1 | 12/2001 | Dubrul et al. | ............ | 606/185 |
| 6,632,197 B2 | 10/2003 | Lyon | ............ | 604/107 |

* cited by examiner

*Primary Examiner*—Michael J. Hayes
*Assistant Examiner*—Nguyen Victor
(74) *Attorney, Agent, or Firm*—Hayes Soloway PC

(57) ABSTRACT

A portal device maintains an opening in the skin of a patient to allow for the passage of surgical device therethrough. Tabs disposed at one end of the portal device may be used to resist removal of the device, retract soft tissue from the operative site, and seal the opening to prevent the escape of gases or liquids.

10 Claims, 17 Drawing Sheets

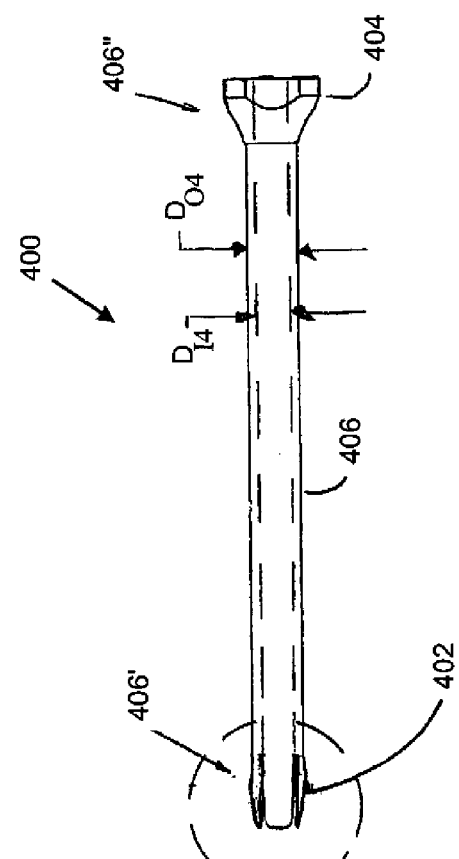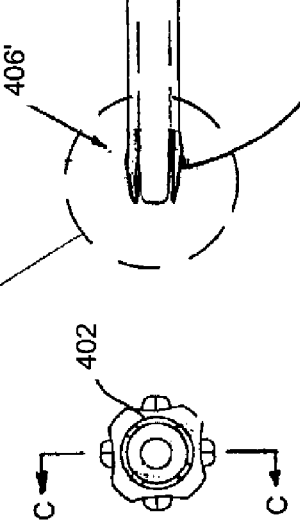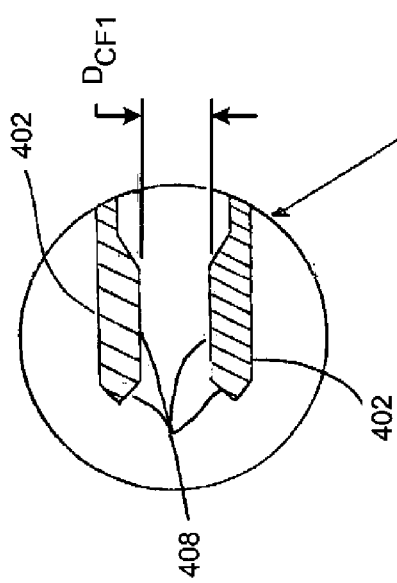
FIG. 6A
FIG. 6B
FIG. 6C

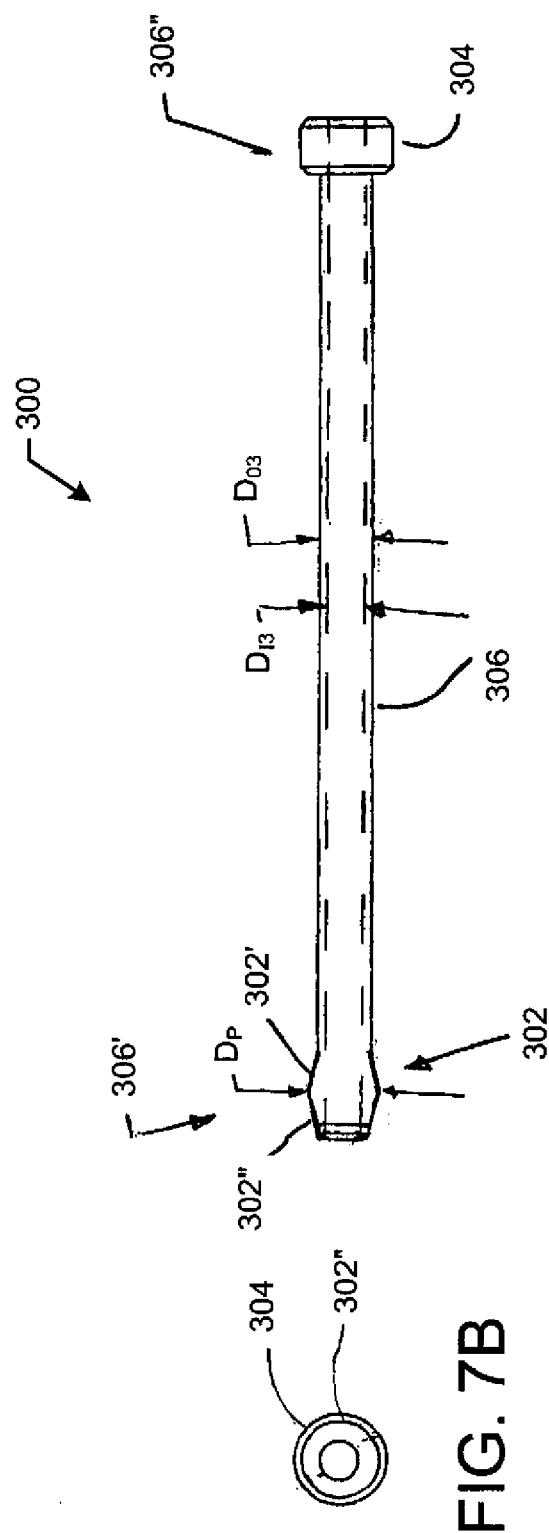

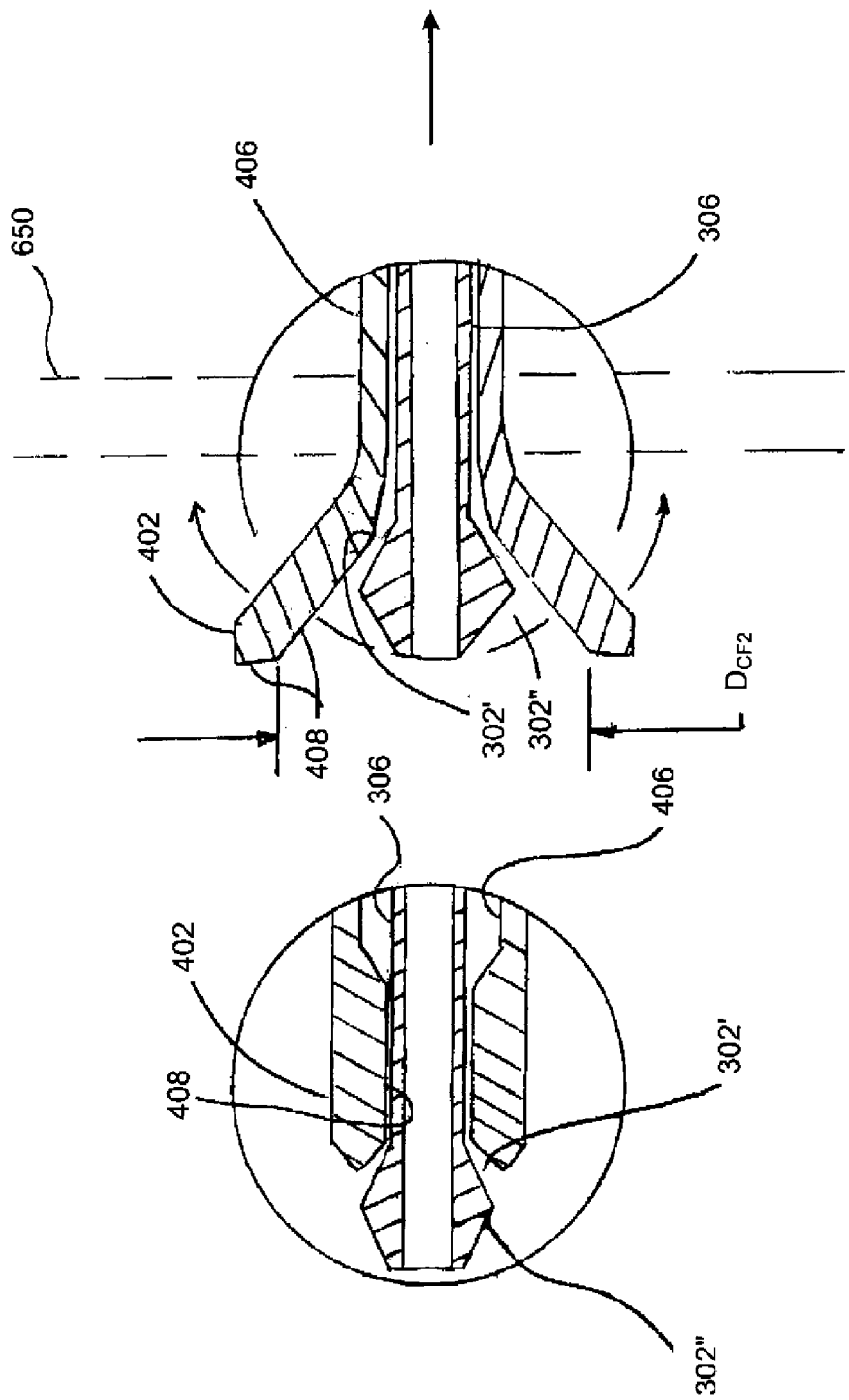

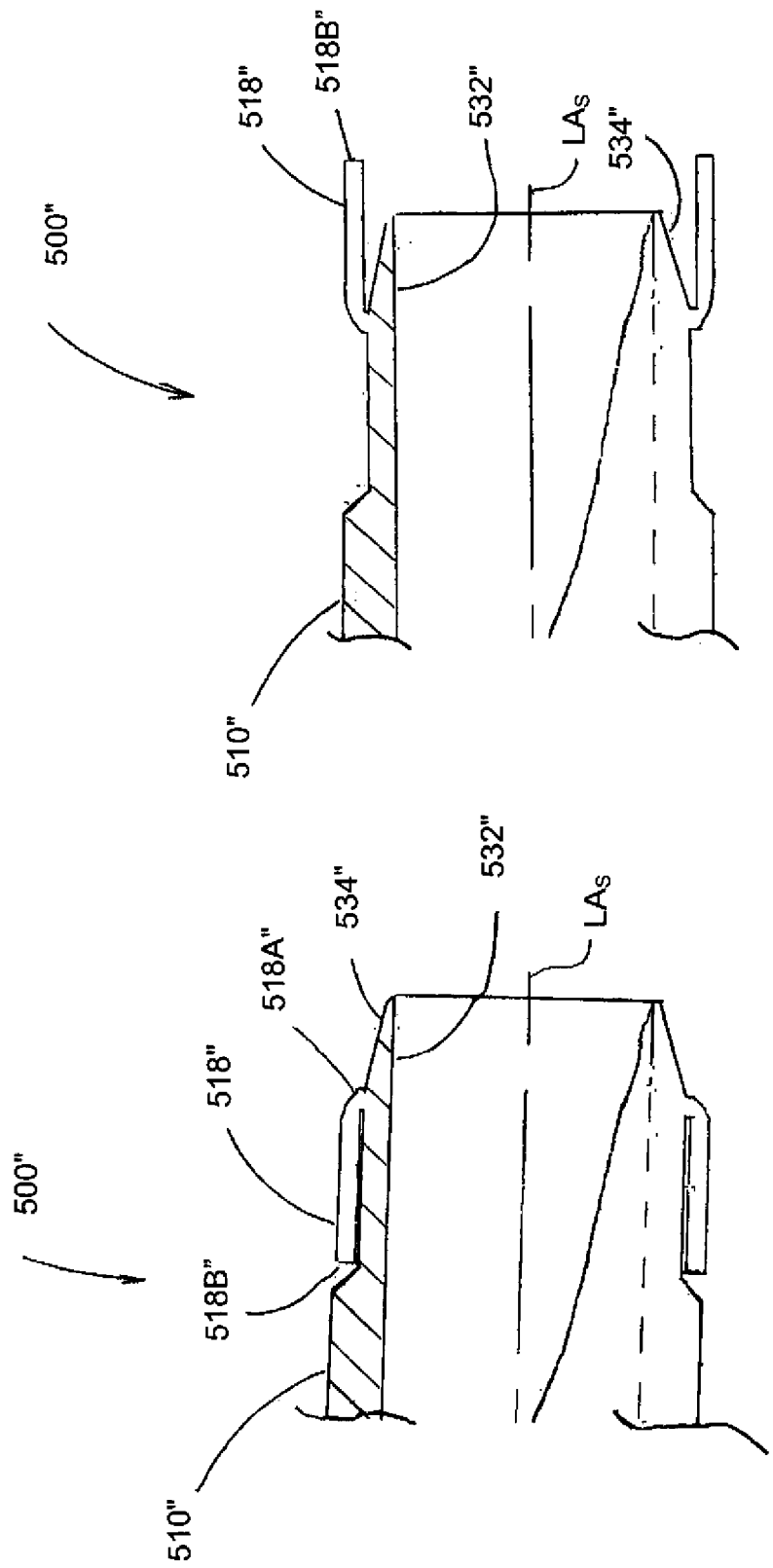

PORTAL DEVICE

CROSS-REFERENCE TO RELATED APPLICATION

This application claims the benefit of copending U.S. provisional patent application Ser. No. 60/377,097 filed on May 2, 2002 and entitled "Portal Device," the teachings of which are incorporated herein by reference in their entirety.

FIELD OF THE INVENTION

The present invention relates generally to a portal device and more particularly to an access port or sleeve for passing surgical instruments into a body.

BACKGROUND OF THE INVENTION

Surgeons routinely perform laproscopic and arthoscopic surgery on different body parts of patients. These types of endoscopic surgeries, or other surgeries where an endoscopic-type opening are maintained, are preferred over conventional surgery due to the lower risk of infection to the patient and quicker recovery times. Creating an opening in the skin of the patient commences the surgery. The opening is maintained by the insertion of a portal device. During the course of the surgery, surgical instruments are repeatedly inserted and removed through the portal device as specific surgical needs arise. A potential problem with the use of these existing portal devices is they typically have smooth outside surfaces that provide little or no resistance to undesirable or untimely removal of the device. If a portal device is inadvertently extracted from an opening in a patient during surgery, this could create clinical or time related problems associated with, for example, replacing, resituating the portal device, or re-sterilizing the portal device. Another problem seen with the existing devices is the unwanted movement into and out of the accessed space, which is a cause for delays or may compromise surgical results.

Therefore, a need has arisen for a portal device that resists removal from an opening and assists with maintaining a clear, unobstructed visual field.

SUMMARY OF THE INVENTION

Embodiments of the present invention provide a system and method for preventing the accidental removal or intra-operative movement of a portal device from an opening in a patient.

Briefly described, one embodiment of the system, among others, can be implemented as follows. A portal device for maintaining an opening in a patient has a first elongated hollow structure having a first end, a second end, and a plurality of cam follower surfaces adjacent the first end. The cam follower surfaces are moveable between a first position, in which the cam follower surfaces form a first interior opening dimension, and a second position, in which the cam follower surfaces form a second and greater interior opening dimension. The portal device further having a second elongated hollow structure with a first end, a second end, and a plurality of cam surfaces adjacent the first end. The second elongated hollow structure is moveable within the hollow portion of the first elongated hollow structure, thereby causing the cam surfaces to urge the cam follower surface to move from the first position to the second position.

The present invention can also be viewed as providing methods for maintaining an opening formed in a patient. In this regard, one embodiment of such a method, among others, can be broadly summarized by the following steps: inserting a first elongated structure and a second elongated structure through an opening and then moving the first elongated structure relative to the second elongated structure, thereby causing an outside dimension of the second structure to increase in size.

Other apparatus, features and advantages of the present invention will be or become apparent to one with skill in the art upon examination of the following drawings and detailed description. It is intended that all such additional apparatus features and advantages be included within this description, be within the scope of the present invention, and be protected by the accompanying claims.

BRIEF DESCRIPTION OF THE DRAWINGS

FIG. 6A is a side view of an outer sheath for use in the portal device of FIG. 1.

FIG. 6B is an end view of the outer sheath of FIG. 6A.

FIG. 6C is an enlarged sectional view of a portion of the outer sheath of FIG. 6A.

FIG. 7A is a side view of an inner sheath for use in the portal device of FIG. 1.

FIG. 7B is an end view of the inner sheath of FIG. 7A.

FIG. 8A is cut-away view of the inner and outer sheaths of FIGS. 6 and 7, where the portal device is in the first position.

FIG. 8B is cut-away view of the inner and outer sheaths of FIGS. 6 and 7, where the portal device is in the second position.

FIG. 16B is a partial sectioned profile view of the sheath shown in FIG. 16A, shown in an "insertion" position.

FIG. 16C is a partial sectioned profile view of the sheath shown in FIG. 16A, shown in a "retraction" position.

DETAILED DESCRIPTION OF THE INVENTION

Figure 1:
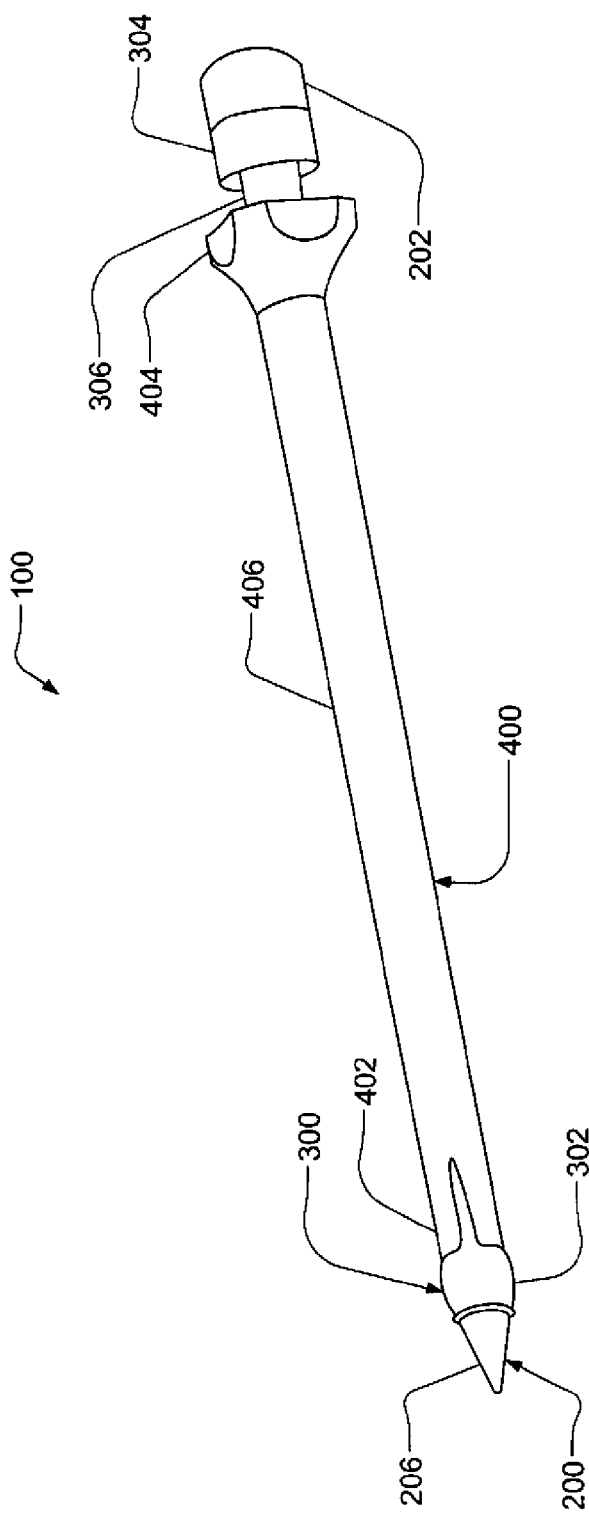
FIG. 1 is a perspective view of a portal device in accordance with a first embodiment of the invention, which is an a first position.
Figure 2:
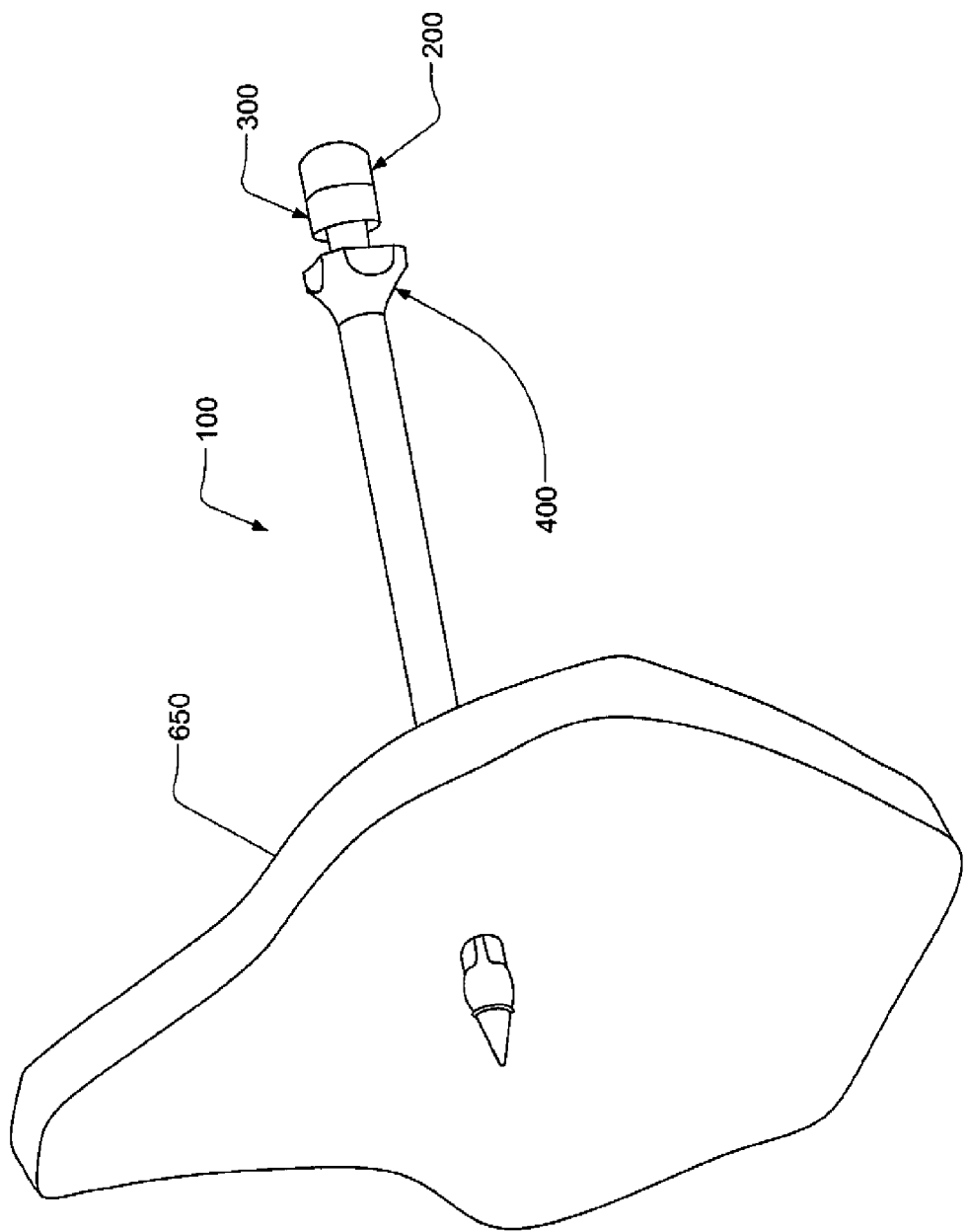
FIG. 2 is a perspective view of the portal device of FIG. 1 after being inserted through skin of a patient.

FIG. 1 shows a first embodiment of a portal device 100 in a first position. The device 100 comprises an obturator 200, an inner sheath 300, and an outer sheath 400. The obturator 200 is preferably made of 17-4 PH SS, while the inner sheath 300 and outer sheath 400 are preferably made of a biocompatible plastic. Other materials that are compatible with living tissue by not being toxic, injurious, or causing immunological reaction may be used without departing from the present invention. FIG. 2 shows the portal device 100 after insertion through the skin 650 of a patient.

Figure 3:
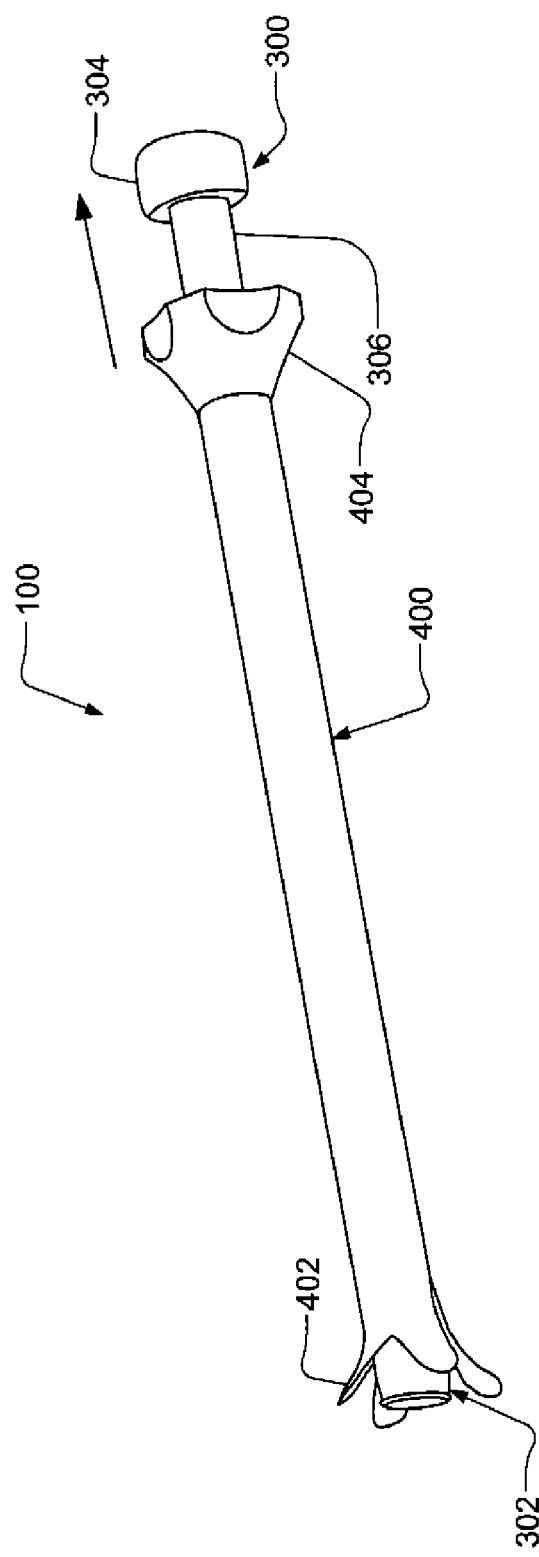
FIG. 3 is a perspective view of the portal device of FIG. 1 in a second position.

FIG. 3 shows the portal device 100 in a second position after the obturator 200 has been withdrawn and flexible tabs 402, to be described in detail in FIGS. 6A-6C, on the outer sheath 400 have been repositioned by a protrusion 302, to be described in detail in FIGS. 7A & 7B, on the inner sheath 300.

Figure 4:
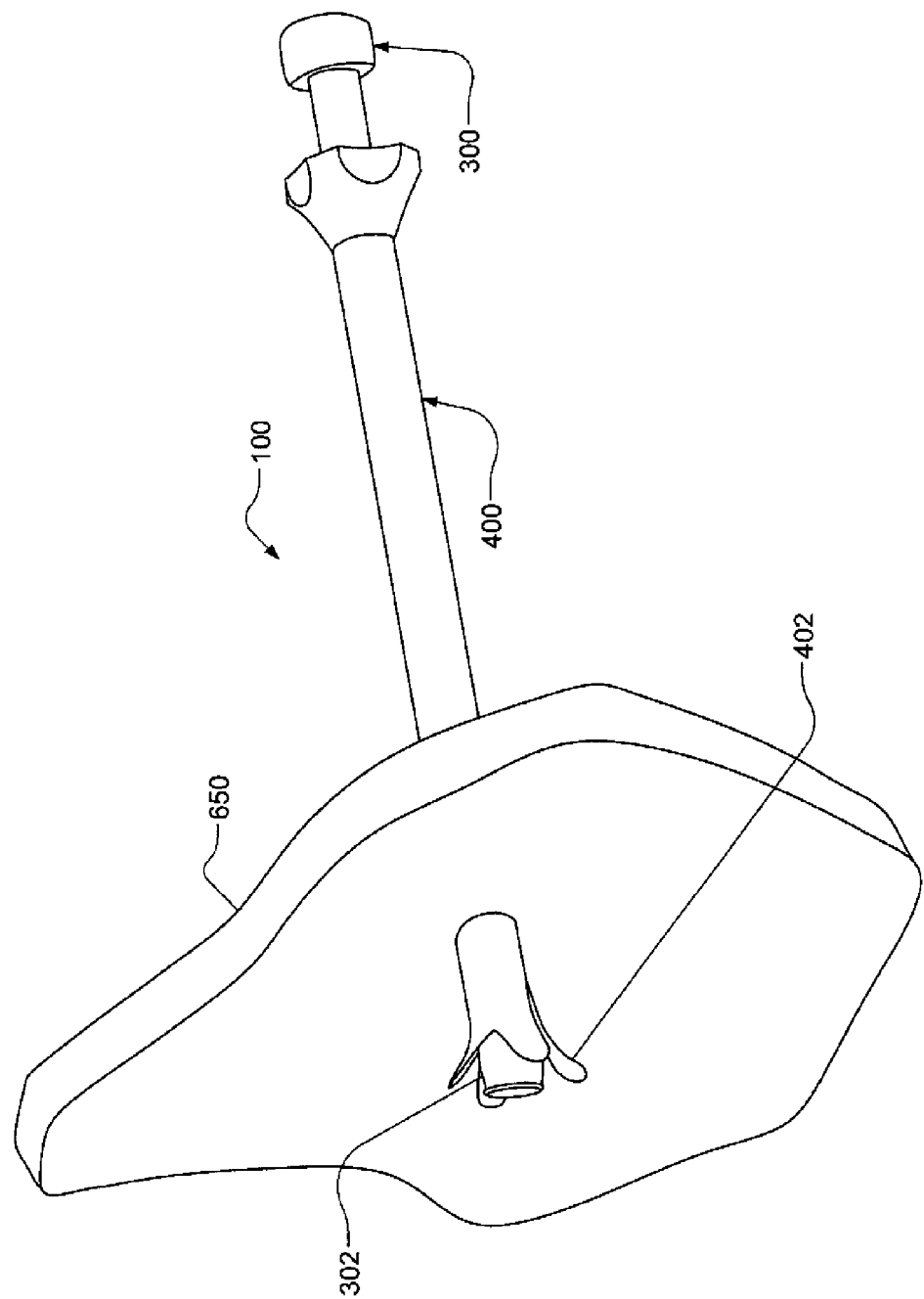
FIG. 4 is a perspective view of the portal device of FIG. 1 in the second position after being inserted through skin of a patient.

FIG. 4 shows the portal device 100 in the second position after being inserted a sufficient distance through skin 650 of a patient. The flexible tabs 402 may be used to resist removal of the inner sheath 300 from the opening in skin 650 and as a tissue retractor to hold soft tissue away from the operative site in order to maintain a clear unobstructed field of view. The tabs 402 may also prevent bodily fluids or other liquids from exiting the opening in skin 650. In certain operations, the cavity may be filled with a gas, for example $CO_2$, and the tabs 402 may be used to seal the opening formed in skin 650 to reduce escape of the gas.

Figure 5:
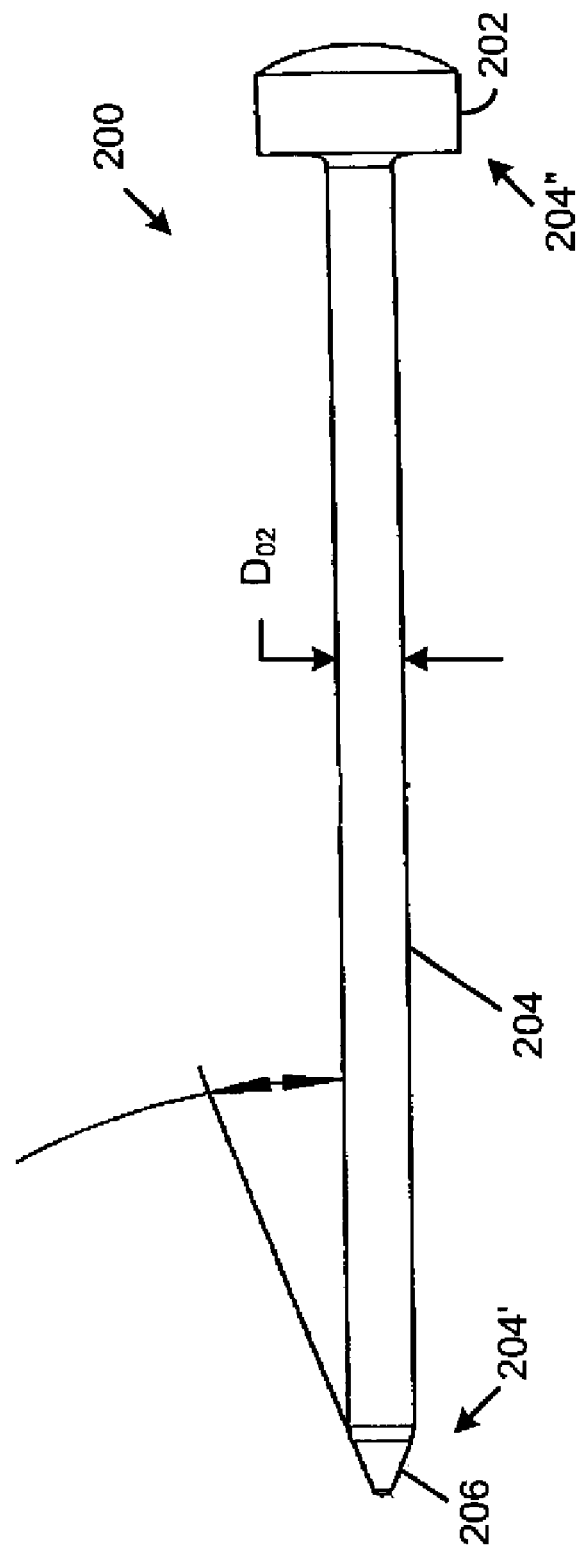
FIG. 5 is a side view of an obturator for use in the portal device of FIG. 1.

FIG. 5 is a side view of the obturator 200. The obturator 200 may comprise an elongated cylindrical portion 204 having a first end 204' and a second end 204". The first end 204' may have a conical portion 206 and the second end 204' may comprise a handle portion 202. The handle portion 202 may prevent the obturator 200 from being inserted too far into the inner sheath 300 and may be used to extract the obturator 200 from the inner sheath 300. An outside dimension $D_{O2}$ of the obturator 200 is sized to fit within an inside dimension $D_{I3}$ of the inner sheath 300 (see FIG. 7A).

FIGS. 6A & 6B are a side view and an end view respectively of the outer sheath 400. The outer sheath 400 may include a first elongated hollow structure 406, preferably a cylinder having an outside dimension $D_{O4}$ and an inside dimension $D_{I4}$. The inside dimension $D_{I4}$ is configured to allow the inner sheath 300 to pass therethrough. The first elongated hollow structure 406 has a first end 406' and a second end 406". The first elongated hollow structure 406 may have a plurality of tabs 402 adjacent the first end 406' and a protrusion 404 adjacent the second end 406". The outer sheath 400 may comprise an area of mechanical weakness formed at the junction of the tabs 402 and the structure 406 to allow the tabs to more easily bend. An area of mechanical weakness may be an area of reduced cross section relative to the surrounding area, an area made of a material having a modulus of elasticity less than the material surrounding it, or other suitable design features that weaken the area relative to the surrounding area. The protrusion 404 may provide a convenient location to grasp the outer sheath 400.

FIG. 6C is an enlarged sectional view of the first end 406' taken through line C-C in FIG. 6B. The tabs 402 have cam follower surfaces 408 formed on an inside surface. The tabs 402 are moveable between a first position as shown in FIGS. 1, 2, 6C, and 8A and a second position as shown in FIGS. 3, 4, and 8B. The cam follower surfaces 408 form a first interior opening dimension $D_{CF1}$ of the first elongated hollow structure 406 when in the first position and a second and greater interior opening dimension $D_{CF2}$ (see FIG. 8B) when in the second position. The shape of the first interior opening dimension preferably is a circle, although other shapes are possible.

FIGS. 7A & 7B are a side view and an end view respectively of the inner sheath 300. The inner sheath 300 may include a second elongated hollow structure 306, preferably a cylinder, having a first end 306' and a second end 306". The elongated structure preferably has an inside dimension $D_{I3}$ and an outside dimension of $D_{O3}$. The second elongated hollow structure 306 is moveable within the hollow portion of the first elongated hollow structure 406. The second elongated hollow structure 306 has a protrusion 302 adjacent the first end 306'. The protrusion 302 may include a plurality of cam surfaces 302' and 302". The cam surfaces 302' and 302" form a first exterior dimension $D_P$. The first exterior dimension $D_P$ preferably is sized smaller than the inside dimension $D_{I4}$ of the elongated hollow structure 406 (see FIG. 6A). The first exterior dimension $D_P$ of the second elongated hollow structure 306 is preferably greater than the first interior opening dimension $D_{CF1}$ (see FIG. 6C) of the first elongated hollow structure 406. A protrusion 304 may be provided adjacent the second end 306" of the second elongated hollow structure 306. The protrusion 304 may provide a convenient location to grasp the inner sheath 300.

To assemble the portal device 100, the first end 204' of the obturator 200 may be inserted through the hollow portion of the second end 306" of the inner sheath 300 and then the first end 306' of the inner sheath 300 and the first end 204' of the obturator 200 are inserted through the hollow portion of the second end 406" of the outer sheath 400.

In an alternative embodiment, the protrusion 304 of the inner sheath 300 is separable from the second end 306" of the inner sheath 300. The second end 306" of the inner sheath 300 may be inserted through the first end 406' of the outer sheath 400 and then the protrusion 304 may be secured to the second end 306" of the inner sheath 300. This design may allow the outside dimension $D_{O3}$ (see FIG. 7A) of the inner sheath 300 to be larger, up to the size of $D_{I4}$ (see FIG. 6A).

In use, the surgeon moves the outer sheath 400 relative to the inner sheath 300 in order to urge the tabs 402 to move from the first position (see FIG. 8A) to the second position (see FIG. 8B). The inner sheath 300 can be moved along a linear path. A spacer may be inserted around the outside of the second elongated structure 306 between the protrusion 304 and the protrusion 404 to maintain the position of the inner sheath 300 relative to the outer sheath 400. Alternatively, a barb may extend out from the second elongated structure 306 when the inner sheath 300 is displaced a predetermined distance relative to the outer sheath 400. To return the portal device 100 to the first position, the surgeon depresses the barb and slides the inner sheath 300 inside the outer sheath 400 or removes the spacer.

In another embodiment, the inside surface of the outer sheath and the outside surface of the inner sheath may comprise cooperating threads. In the case of this latter embodiment, to move the inner sheath 300 relative to the outer sheath 400, the surgeon rotates the inner sheath 300 relative to the outer sheath 400.

Figure 9A:
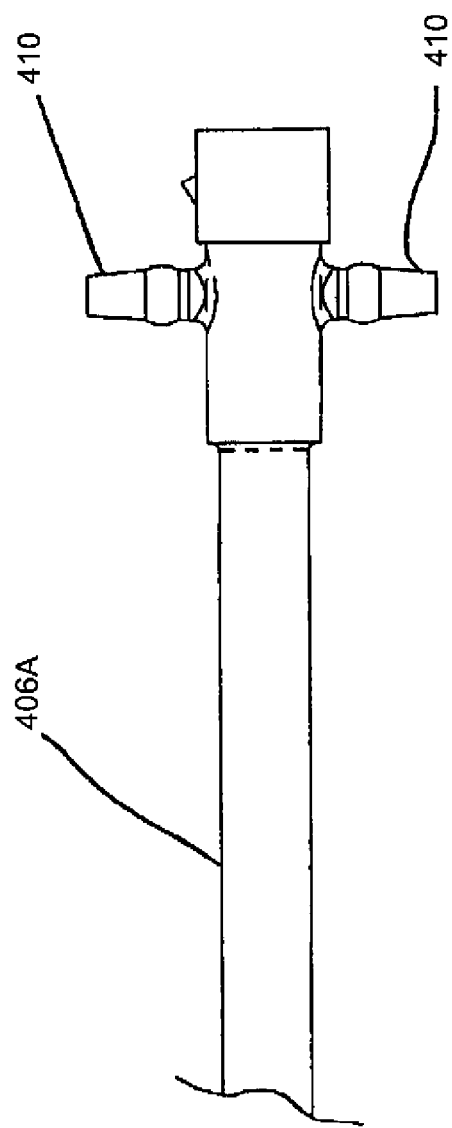
FIG. 9A is a side view of an end portion of an outer sheath associated with a portal device, in accordance with a second embodiment of the invention.
Figure 9B:
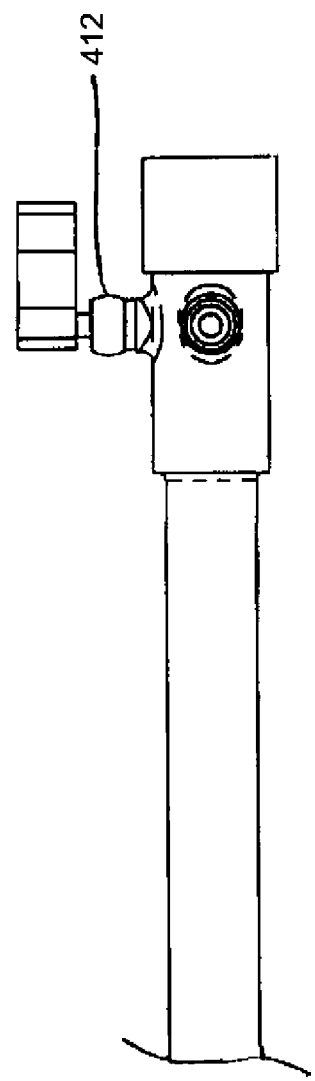
FIG. 9B is a view of the outer sheath of FIG. 9A rotated 90° about a horizontal axis.

FIG. 9A is a side view of an end portion of an outer sheath 406A of a portal device. The outer sheath 406A may include a Luer connection 410. FIG. 9B is a view of the end portion of the outer sheath 406A shown in FIG. 9A showing a shut off valve 412 for the Luer connection 410.

Figure 10A:
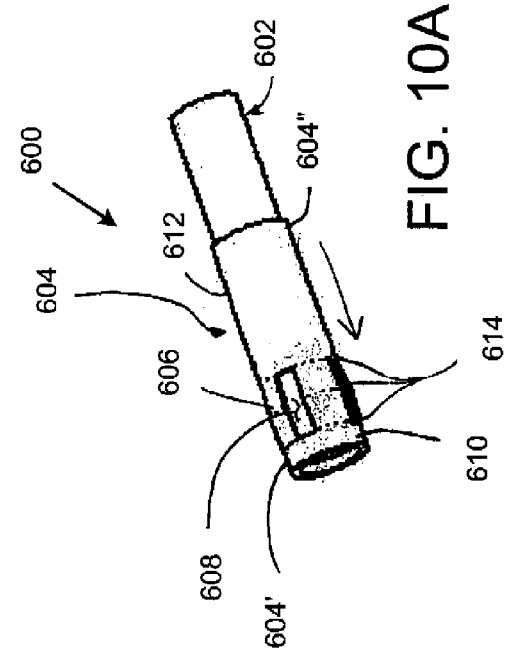
FIGS. 10A-D show a portal device in accordance with a third embodiment of the invention as the portal device progresses from an "insertion" position to an "extended" position.
Figure 10B:
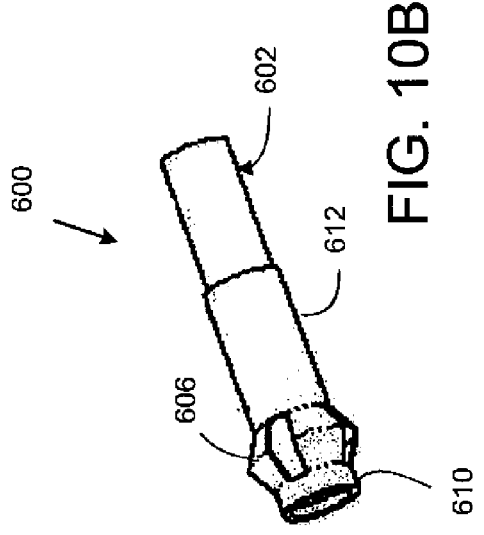
Figure 10C:
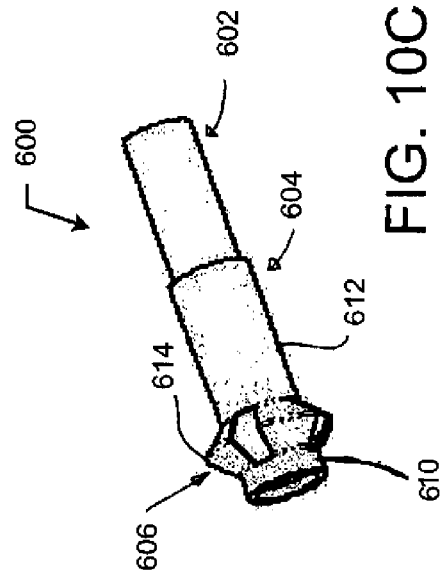
Figure 10D:
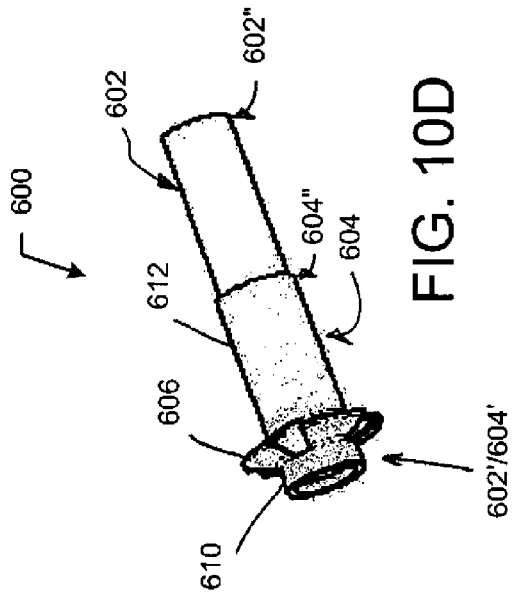

FIGS. 10A-10D show the transformation of a portal device 600. The device includes an inner sheath 602 and an outer sheath 604. The inner sheath 602 and the outer sheath 604 may comprise hollow elongated structures, preferably a hollow cylinder. The outer sheath 604 has a first end 604' and a second end 604" and the inner sheath has a first end 602' and a second end 602". FIG. 10A shows the portal device 600 in a first configuration. The portal device 600 is inserted through skin 650 of a patient in the first configuration. An obturator (not shown) may be used to assist in the insertion of the device 600 through an opening in the skin 650. The obturator is configured to fit within the hollow portion of the inner sheath 602. The outer sheath 604 may comprise a plurality of tabs 606 disposed between a first ring 610 and a second ring 612. The tabs 606 may be separated by a plurality of gaps 608. As the second end 604" of the outer sheath 604 is moved relative to the inner sheath 602, the tabs 606 begin to fold about an area of mechanical weakness 614. Movement of the second end 604" of the outer sheath 604 relative to the second end 602" of the inner sheath 602 increases the dimension across the tabs 606 from $D_6$ to $D_{6'}$ (see FIG. 11 and FIG. 12 respectively). The increase in dimension may make it more difficult to extract the device 600 from the opening in the skin 650. The device 600 may be made from biocompatible material.

Figure 11:
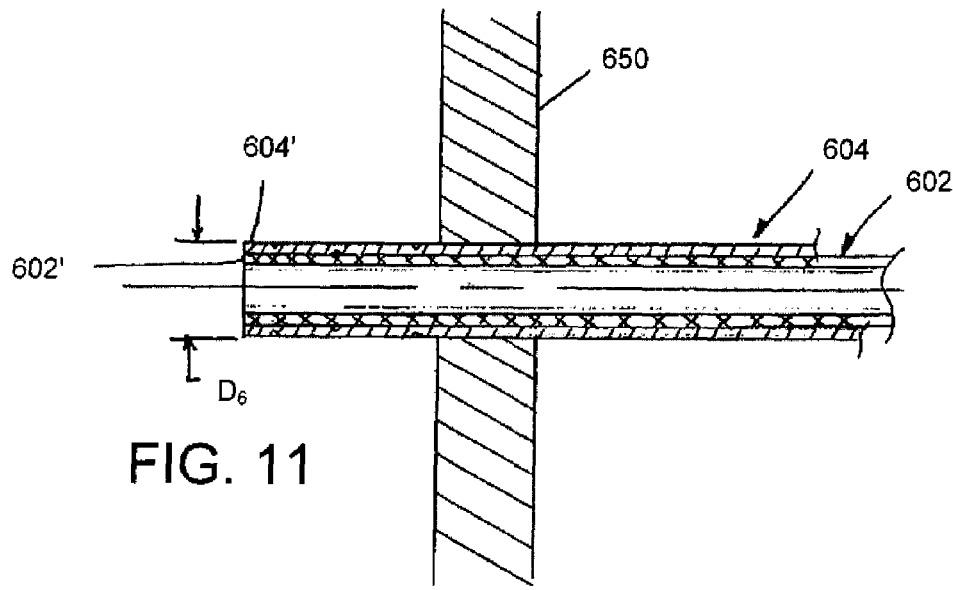
FIG. 11 is a profile view of the portal device shown in FIG. 10A, inserted through skin of a patient.
Figure 12:
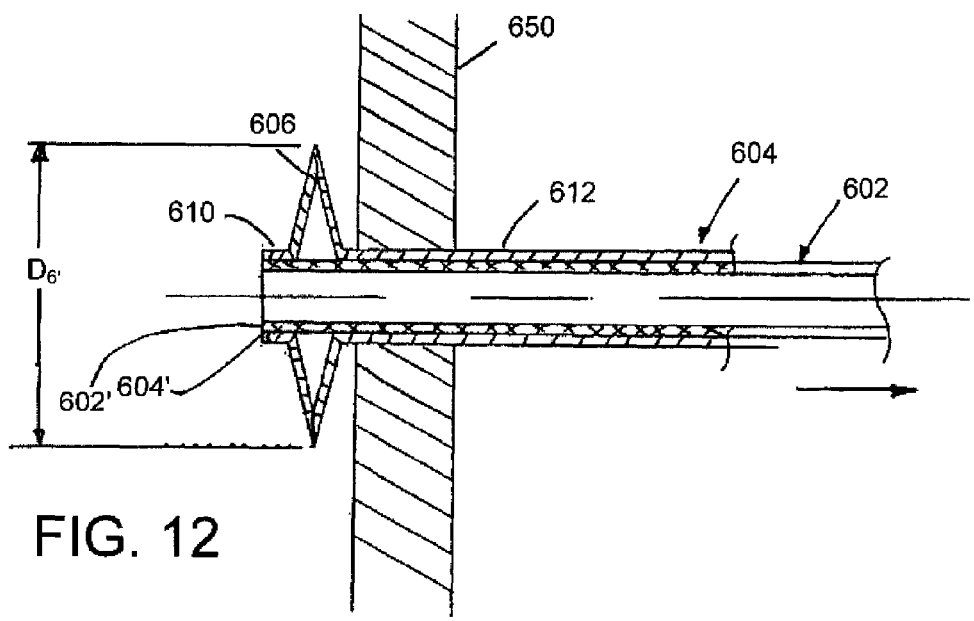
FIG. 12 is a profile view of the portal device shown in FIG. 10D.

FIG. 11 shows a profile view of the device 600 as it is inserted or removed from the opening in the skin 650 and FIG. 12 shows a profile view of the device 600 in a "deployed" configuration. In the "deployed" configuration, the tabs 606 may be used to resist removal of the portal device 600, retract soft tissue from the operative site, and seal the opening to prevent the escape of gases or liquids. The device is capable of being reconfigured from an "insert" configuration to the "deployed" configuration numerous times. In the embodiment shown, the movement of the inner sheath relative to the outer sheath is along a linear path.

A locking mechanism may be employed to keep the second end 604" of the outer sheath 604 spaced from the second end 602" of the inner sheath 602 without the application of force by the surgeon.

When the surgery is complete, the device 600 can be returned to the first configuration (see FIG. 10A), thereby facilitating easy removal of the device from the opening in the skin 650.

The first end 602' of the inner sheath may be coupled to the first end 604' of the outer sheath 604 by an adhesive or mechanical bond, a mechanical fastener, or a combination thereof.

Figure 12A:
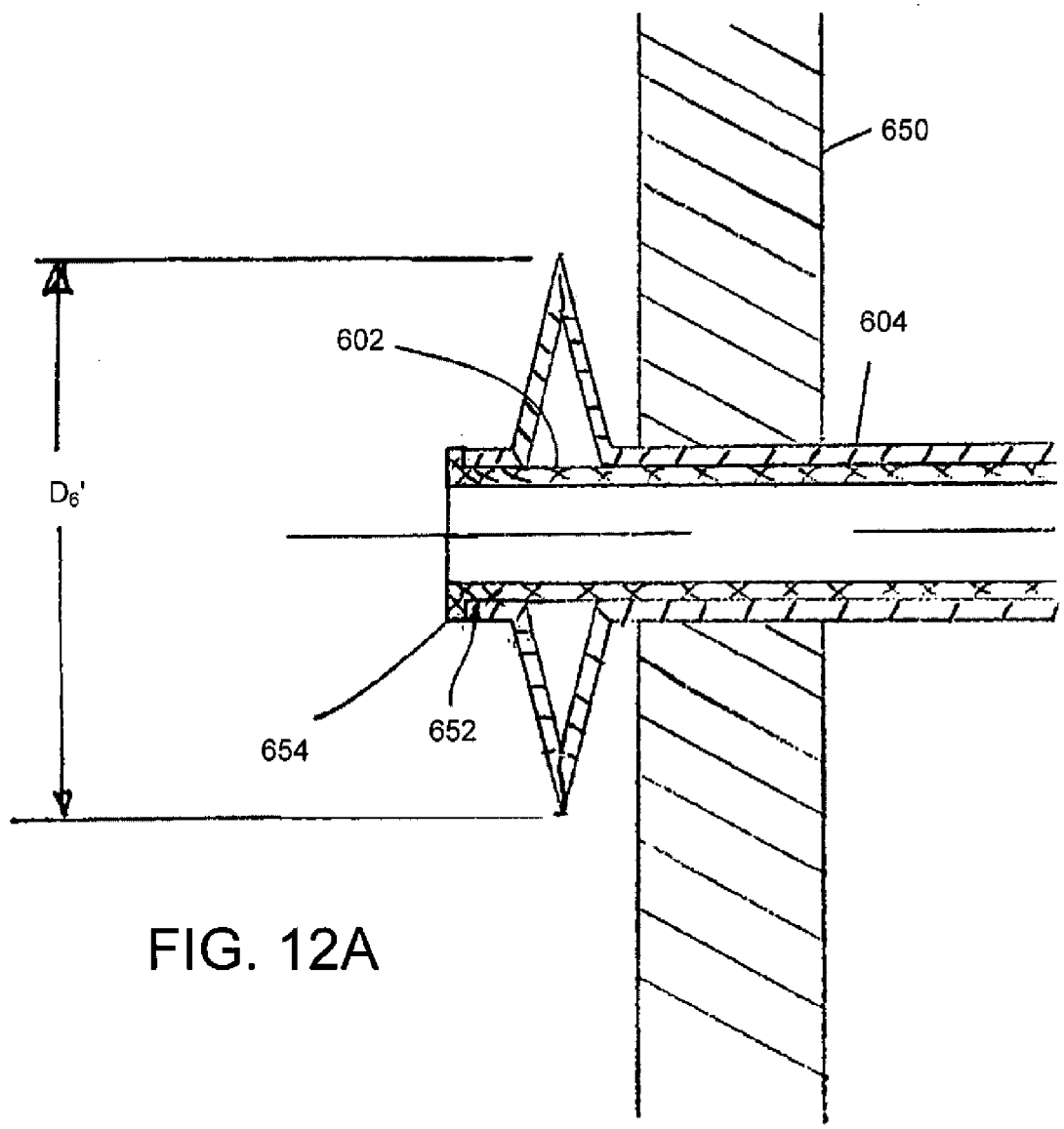
FIG. 12A is a profile view of a portal device in accordance with a fourth embodiment of the invention.

FIG. 12A shows a fourth embodiment portal device. As shown in FIG. 12A, the inner sheath has a lip 654 adjacent the first end 602 that engages with a first end 652 of the outer sheath 604 to couple the inner sheath to the outer sheath.

In an alternative embodiment, the inside surface of the outer sheath 604 and the outside surface of the inner sheath 602 may comprise cooperating threads. To move the inner sheath 602 relative to the outer sheath, the surgeon may rotate the inner sheath 602 relative to the outer sheath 604.

Figure 13A:
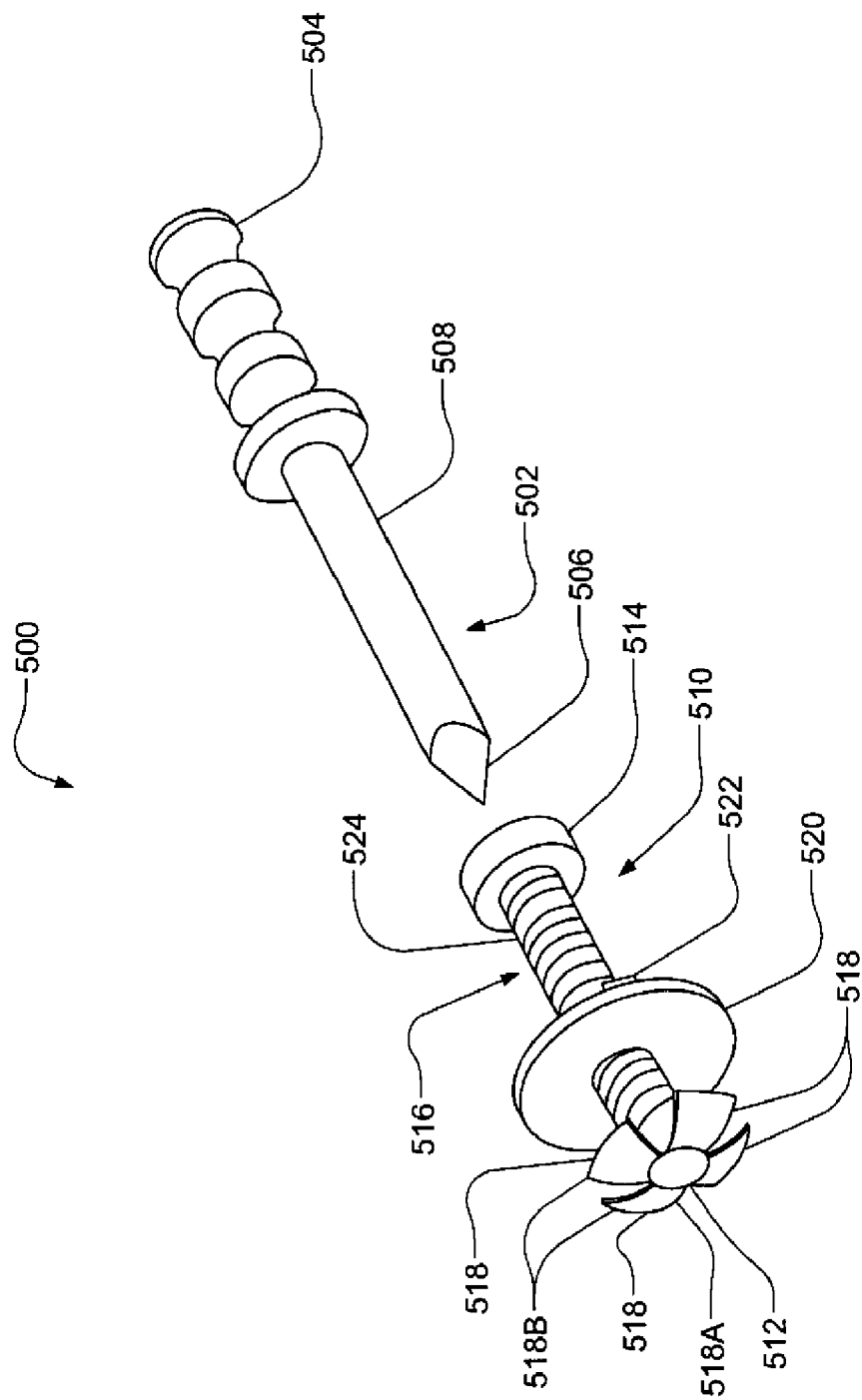
FIG. 13A is a perspective view of a portal device in accordance with a fifth embodiment of the invention.
Figure 13B:
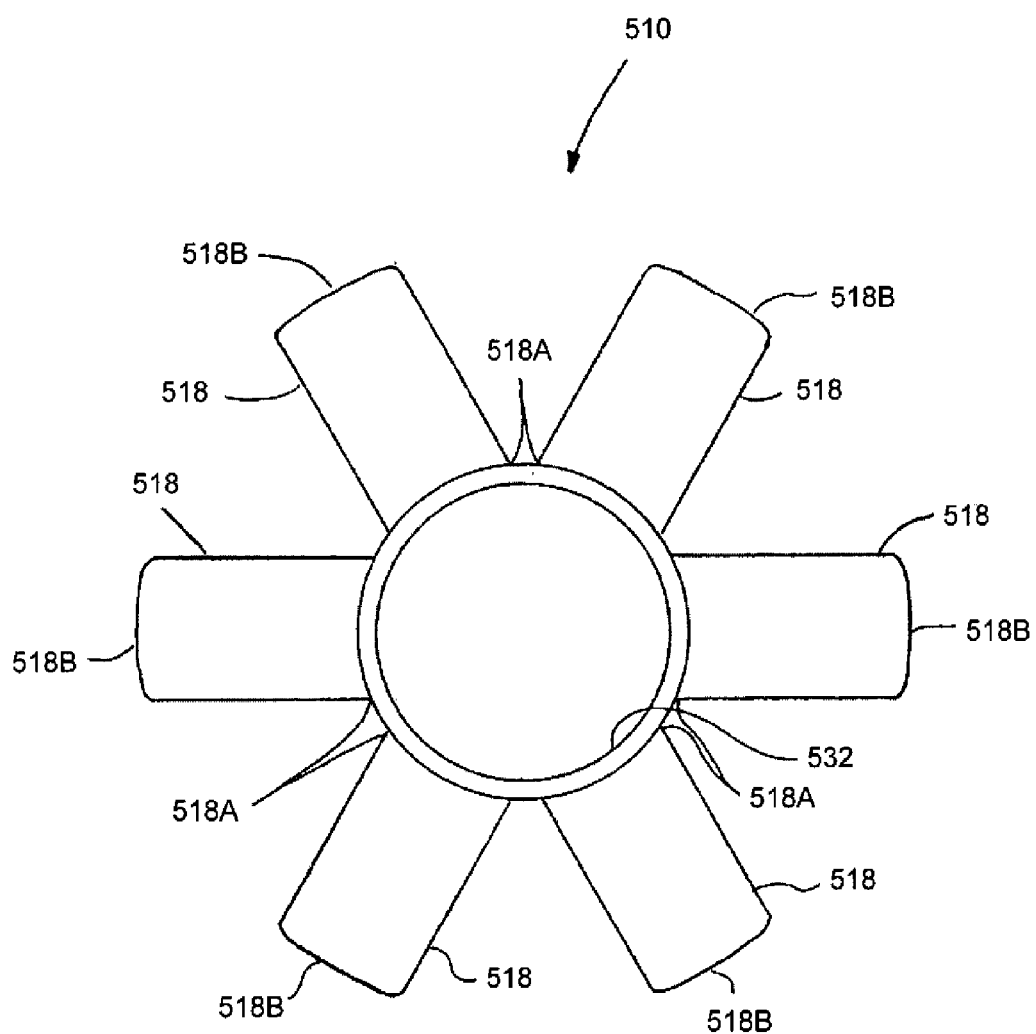
FIG. 13B is an end view of the portal device shown in FIG. 13A.

FIG. 13A shows a portal device 500 including a sheath 510, a probe 502, and a plate 520. The device 500 may be made from a biocompatible material. The sheath 510 may have a first end 512, a middle portion 516, and a second end 514. The middle portion 516 may have an externally formed thread 524. An opening 532 may extend from the first end 512 to the second end 514 and may be sized to allow the probe 502 to extend therethrough. A plurality of tabs 518 may extend generally radially outward from the first end 512 of the sheath 510 as shown in FIG. 13B. The tabs 518 are coupled to the sheath 510 and bend about a base 518A. The tabs 518A may have an area of reduced mechanical strength at the base 518A. Ends 518B of the tabs 518 may be capable of flexing towards or away from the second end 514. The probe 502 includes a first end having a lead-in 506, a body portion 508, and a handle end 504.

The plate 520 may be circular in cross section, although other shapes will work, and include an internal thread that cooperates with the external thread 524 on the middle portion 516 on the sheath 510. The plate 520 may have wings 522 to assist in rotating the plate 520. The plate 520 may be made of a polymeric material.

With the probe 502 inserted in the sheath 510, a surgeon may insert the portal device 500 into an opening formed in the skin. The lead-in 506 urges the opening to increase in size. As the sheath 510 is inserted into the opening in the skin, the ends 518B of the tabs 518 fold towards the second end 514 of the sheath 510. After the sheath has been inserted through the skin far enough to allow the tabs 518 to return to their original position, the sheath may be extracted slightly until the tabs 518 contact the inside surface of the skin. The probe 502 may then be removed. In this configuration, the tabs 518 may be used to resist removal of the sheath 510, retract soft tissue from the operative site, and seal the opening to prevent the escape of gases or liquids. The surgeon may then rotate the plate 520 by applying a rotative force to the wings 522 on the plate 520. The surgeon may rotate the plate 520 until the plate 520 comes into contact with the outside surface of the skin. Surgical devices may now be passed through the sheath 510.

When the surgery is complete, the surgeon may apply a force along the longitudinal axis of the sheath 510 away from the skin causing the ends 518B of tabs 518 to fold away from the second end 514 of the sheath 510, the tabs 518 bending about the base 518A.

Figure 14:
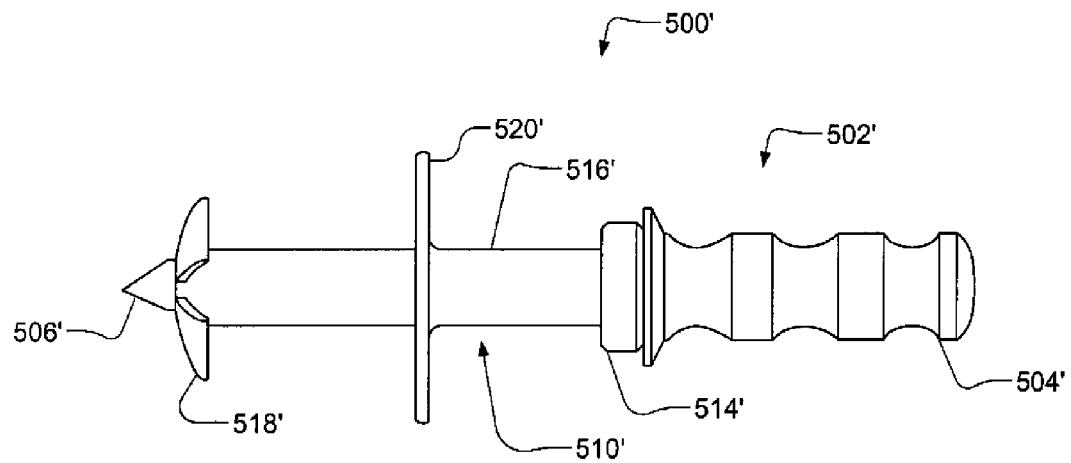
FIG. 14 is a profile view of a portal device in accordance with a sixth embodiment of the invention.
Figure 15:
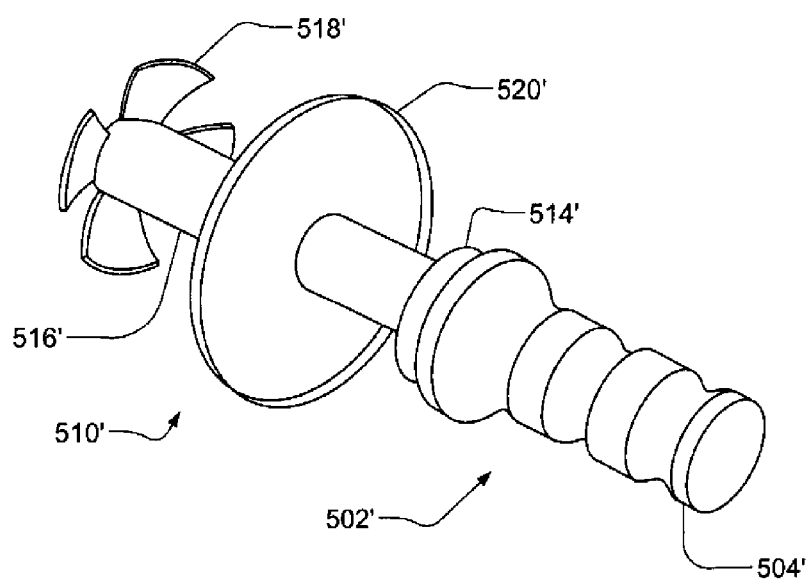
FIG. 15 is a prospective view of the portal device shown in FIG. 14.

FIG. 14 is a profile view of a sixth embodiment portal device 500' and FIG. 15 is a perspective view of the sixth embodiment portal device 500'. It should be noted that the reference numerals from FIG. 13 have been reused in FIG. 14 and FIG. 15 and a "'" has been added for similar components. The device may be similar in operation to the portal device 500 except a plate 520' slides along the sheath 510'.

Figure 16A:
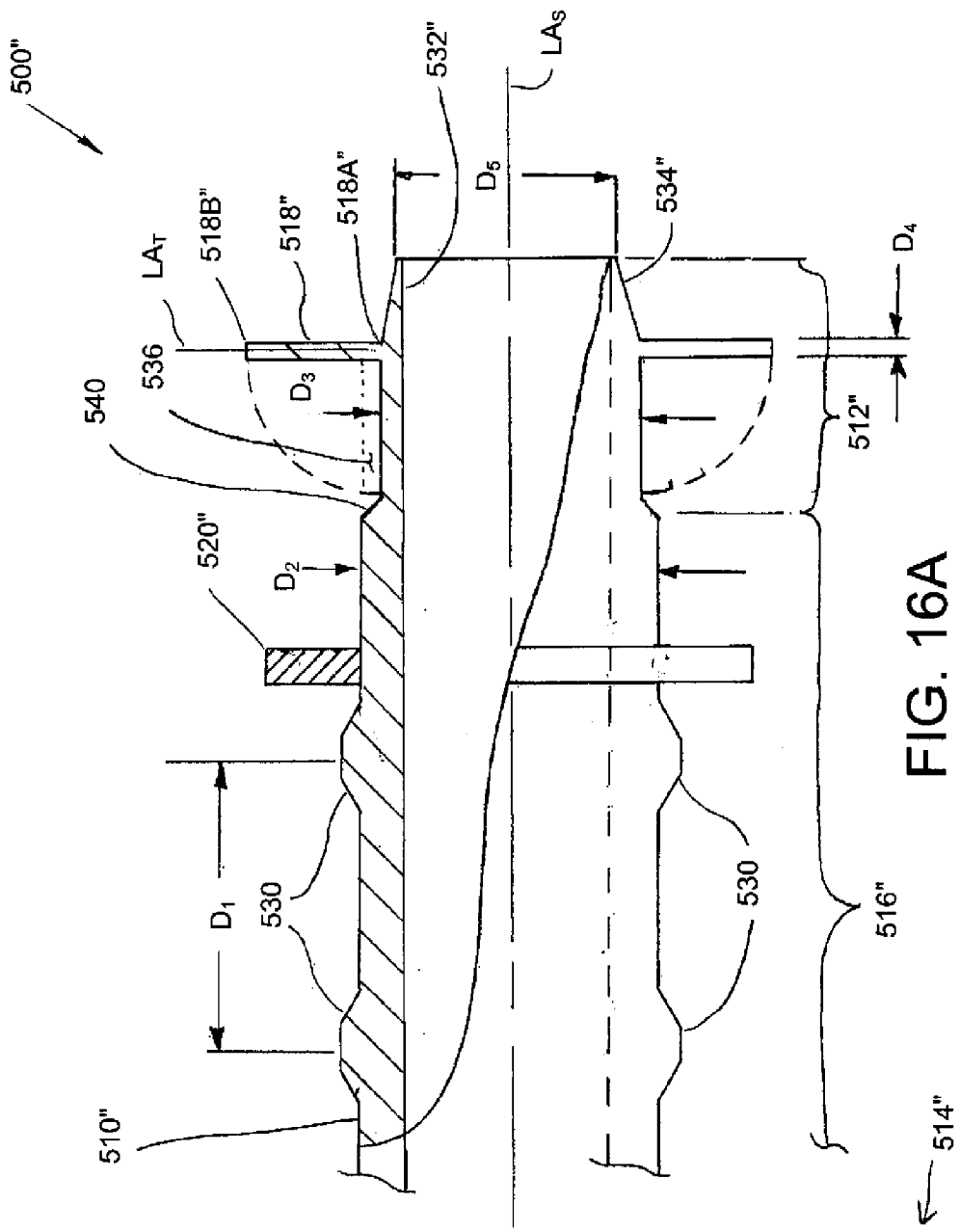
FIG. 16A is a sectioned profile view of a sheath associated with a portal device in accordance with a seventh embodiment of the invention, shown in a "neutral" position.

FIG. 16A shows a sectioned profile view of a sheath 510" of a portal device 500" in a "neutral" position. The sheath 510" may be made from a biocompatible material. The sheath 510" may have a first end 512", a middle portion 516", and a second end 514" (not shown). The second end may be similar to the second end 514' shown in FIG. 14.

An opening 532" may extend from the first end 512" to the second end 514" and may be sized to allow a probe to extend therethrough. The probe may be similar to the probe 502 shown in FIG. 13. A plurality of tabs 518" may extend generally radially outward from the end 512" of the sheath 510".

In the "neutral" position, the tabs 518" may be used to resist removal of the sheath 510", retract soft tissue from the operative site, and seal the opening to prevent the escape of gases or liquids. The tabs 518" may be generally linear, as shown in FIG. 16A, or may be arcuate, as shown in FIG. 14. The tabs 518" may have a thickness "$D_4$". The tabs 518" are coupled to the sheath 510" at a base 518A". An area of mechanical weakness may exist in close proximity to the base 518A" to allow an opposing end 518B" of the tabs 518" to folds towards the second end 514", as shown in FIG. 16B, or away from the second end 514", as shown in FIG. 16C.

The first end 512" may have a lead-in 534" having a first dimension "$D_5$". The sheath 510" may have a dimension "$D_3$" from the tab 518" to a transition region 540. The transition region 540 may transition the profile of the sheath 510" from the dimension "$D_3$" to a dimension "$D_2$" of the middle portion 516". When the tab 518" folds about the base 518A" and the opposing end 518B" of the tab 518" folds towards the second end 514" of the sheath 510", (see FIG. 16B), a longitudinal axis $LA_T$ of the tabs 518" lies generally parallel with a longitudinal axis $LA_S$ of the sheath 510". The difference between the dimension "$D_2$" of the middle portion 516" and the dimension "$D_3$" of the first end 510" ($D_2$–$D_3$) is preferably approximately the thickness "$D_4$" of the tab 518".

The middle portion 516" of the sheath 510" may have a plurality of outwardly extending protuberances 530 spaced by a distance "$D_1$". Disposed along the outside surface of the sheath 510" may be a plate 520". The plate 520" may be circular in cross section, although other shapes will work. The plate 520" may have an opening formed therein that allows the plate 520" to slide along the longitudinal axis $LA_S$ of the sheath 510", the outwardly extending protuberances 530 providing resistance to free movement of the plate 520". The plate 520" may be made of a pliable material to allow the surgeon to slide the plate 520" over the protuberances 530 of the sheath 510" to a desired position. The plate 520" may be moved along the longitudinal axis $LA_S$ of the sheath 510" to resist movement of the sheath 510" into the opening in the patient.

With a probe inserted in the sheath 510", a surgeon may insert the portal device 500" into an opening formed in the skin. The lead-in 534" urges the opening to increase in size. As the sheath 510' is inserted into the opening in the skin, the ends 518B" of the tabs 518" fold about the base 518A" towards the second end 514" of the sheath 510" (see FIG. 16B). After the sheath 510" has been inserted through the skin far enough to allow the tabs 518" to return to the "neutral" position (see FIG. 16A), the sheath 510" may be extracted slightly until the tabs 518" contact the inside surface of the skin. The probe may then be removed. The surgeon may then position the plate 520" along the sheath 510" by sliding the plate 520" along the longitudinal axis $LA_S$ of the sheath 510". Surgical devices may now be passed through the sheath 510".

When the surgery is complete, the surgeon may apply a force along the longitudinal axis $LA_S$ of the sheath 510" away from the patient's skin. The tissue surrounding the opening causes the ends 518B" of tabs 518" to fold about the base 518A" and away from the second end 514" of the sheath 510" (see FIG. 16C), to allow the sheath 510" to be removed from the opening.

Thus, it is apparent that there has been provided a portal device that satisfies the objectives set forth herein. Those skilled in the art will appreciate still other modifications and variations of the present invention are possible in light of the above teaching. It is, therefore, to be understood that within the scope of the appended claims, the invention may be practiced otherwise than literally described, but fail within the scope therein.

We claim:

1. A portal device for maintaining an opening in a patient, comprising:
   a first elongated hollow structure having a first end and a second end, the first elongated hollow structure having a plurality of cam follower surfaces adjacent the first end, the cam follower surfaces being moveable between a first position and a second position, the cam follower surfaces forming a first interior opening dimension of the first elongated hollow structure when the cam follower surfaces are in the first position and a second and greater interior opening dimension when the cam follower surfaces are in the second position; and
   a second elongated hollow structure having a first end and a second end, the second elongated hollow structure being moveable within the first elongated hollow structure, the second elongated hollow structure having a plurality of cam surfaces adjacent the first end, the cam surfaces forming a first exterior dimension of the second elongated hollow structure, the first exterior dimension being greater than the first interior opening dimension of the first elongated hollow structure.

2. The portal device of claim 1, wherein movement of the first elongated hollow structure relative to the second elongated hollow structure urges the cam surfaces to contact the cam follower surfaces.

3. The portal device of claim 2, wherein movement of the first elongated hollow structure relative to the second elongated hollow structure urges the interior opening dimension to increase in size.

4. The portal device of claim 1, further comprising an obturator sized to fit within the second elongated hollow structure.

5. The portal device of claim 4, wherein the obturator comprises a conical or trocar end.

6. The portal device of claim 1, wherein movement of the first elongated hollow structure relative to the second elongated hollow structure is along a linear path.

7. The portal device of claim 1, wherein movement of the first elongated hollow structure relative to the second elongated hollow structure is along a helical path.

8. The portal device of claim 1, wherein an exterior dimension of the first elongated hollow structure in the second position is greater in size than the exterior dimension of the first elongated hollow structure in the first position.

9. The portal device of claim 1, wherein the exterior dimension of the first elongated hollow structure in the second position is greater in size than an initial opening formed in the skin of the patient.

10. The portal device of claim 1, wherein the first elongated hollow structure comprises a hollow cylinder.

* * * * *